United States Patent [19]

Burggraaf et al.

[11] Patent Number: 4,770,761

[45] Date of Patent: Sep. 13, 1988

[54] SENSOR FOR DETERMINING THE OXYGEN CONTENT IN A GAS

[75] Inventors: Anthonie J. Burggraaf, Boekelo; Maarten J. Verkerk, Eindhoven, both of Netherlands

[73] Assignee: U.S. Philips Corporation, New York, N.Y.

[21] Appl. No.: 595,784

[22] Filed: Apr. 2, 1984

Related U.S. Application Data

[63] Continuation of Ser. No. 438,830, Nov. 3, 1982, abandoned.

[30] Foreign Application Priority Data

Nov. 12, 1981 [NL] Netherlands ............... 8105116

[51] Int. Cl.⁴ ............................. G01N 27/58
[52] U.S. Cl. ................... 204/425; 204/421; 204/424
[58] Field of Search ............... 338/34; 204/421, 424, 204/425, 426, 427, 428, 429, 1 S, 1 T, 408

[56] References Cited

U.S. PATENT DOCUMENTS

| | | | |
|---|---|---|---|
| 3,691,023 | 9/1972 | Ruka et al. | 204/1 T |
| 4,071,817 | 1/1978 | Bahl | 204/1 S X |
| 4,224,113 | 9/1980 | Kimura et al. | 204/425 X |
| 4,233,033 | 11/1980 | Eifler et al. | 338/34 X |
| 4,259,292 | 3/1981 | Ichinose et al. | 338/34 X |
| 4,264,425 | 4/1981 | Kimura et al. | 204/425 X |
| 4,302,312 | 11/1981 | Ishitani et al. | 204/426 X |
| 4,304,652 | 12/1981 | Chiba et al. | 204/425 |
| 4,322,383 | 3/1982 | Yasuda et al. | 338/34 X |
| 4,345,985 | 8/1982 | Tohda et al. | 204/425 X |
| 4,472,262 | 9/1984 | Kondo et al. | 204/425 X |

FOREIGN PATENT DOCUMENTS 2918932 11/1979 Fed. Rep. of Germany ...... 204/426

OTHER PUBLICATIONS

Subbano E. C., Solid Electrolytes and their Applications, NY, Plenum Press, 1980, pp. 35-49.

Primary Examiner—John F. Niebling
Assistant Examiner—Nam X. Nguyen
Attorney, Agent, or Firm—Paul R. Miller

[57] ABSTRACT

A sensor is described for determining the oxygen content of a gas with the sensor consisting of a tablet of stabilized bismuth trioxide having electrode coatings on opposite major surfaces. The resistance between the electrode coatings is a measure of an oxygen partial pressure-dependent quantity. The tablet is immersed entirely in the gas to be analyzed so that the nesessity of a reference gas is eliminated.

14 Claims, No Drawings

SENSOR FOR DETERMINING THE OXYGEN CONTENT IN A GAS

This application is a continuation of Ser. No. 438,830, filed Nov. 3, 1982, now abandoned and the benefits of such parent application are hereby claimed.

The invention relates to a sensor for determining the oxygen content in a gas.

Such sensors are known (for example from German Offenlegungsschrift No. 2742278) in which a solid electrolyte which shows ion conductivity is used in the form of a partition provided on both sides with electrode coatings. Gas having a known oxygen content is present as a reference gas on one side of the partition, and gas in which the oxygen is present in an unknown concentration is present on the other side. As a result of this a potential difference is established between the two electrode coatings, which produces a current through the material which is transported by the oxygen ions in the solid electrolyte. This current has a value which is proportional to the ratio of the oxygen concentrations on the two sides of the partition and hence the unknown oxygen concentration can thus be calculated.

The mobility of the ions in the solid electrolyte depends considerably on the temperature and a consequence of this temperature dependence is that the oxygen determination also has a temperature-dependent sensitivity. During the measurement the temperature of the solid electrolyte in practice must at least be 250° C.

A disadvantage of this known type of oxygen sensor is that a reference gas having an oxygen concentration which is kept accurately constant is essential.

It is the object of the invention to provide a sensor which operates without using such a reference gas.

According to the invention, the sensor of the above-described type using a solid electrolyte with ion conductivity which is provided on both sides with electrode coatings is characterized in that the solid electrolyte consists of stabilised $Bi_2O_3$ in the form of a tablet which comprises electrode coatings and is surrounded entirely by the gas to be analyzed and that the resistance between the electrode coatings is measured as an oxygen partial pressure-dependent quantity.

The $Bi_2O_3$ is stabilised in known manner by the addition of yttrium oxide, an oxide of an element from the lanthanide group having an atomic number between 62 and 70 and including the terminal values of niobium oxide, tantalum oxide or tungsten oxide. As a result of stabilisation the material obtains a face-centred cubic lattice and only in this structure can it be used as a sensor.

The operation of the sensor according to the invention is based on the variation of the electrode resistance as a function of the oxygen partial pressure. By means of a direct current voltage the resistance of the electrode/electrolyte combination is measured. For this it holds that:

$$R_{electrode} = R_{total} - R_{electrolyte} = K \cdot P_{O_2}^n$$

$R_{total}$ is the quantity to be measured;

$R_{electrolyte}$ and also K are quantities which are independent of the oxygen partial pressure and a known function of the temperature. With the choice of a definite temperature, both are constants. In this case also the measurement must thus be carried out at a particular temperature must thus be carried out at a particular temperature which is kept constant.

This applies to a certain chosen electrode morphology; K as well as the exponent n in the above equation depend on the electrode morphology. For a gauze electrode, for example, $n = -\frac{3}{4}$ and for a sputtered electrode $n = -\frac{1}{2}$.

With a correct choice of the electrode morphology and the dimensions of the tablet, the resistance value of the electrolyte is small with respect to the overall resistance and may then be neglected. The measuring range within which reliable values can be obtained depends on the chosen combination of temperature/oxygen partial pressure of the sensor and of the nature of the electrodes and generally is in the temperature range from 500° to 800° C. and a range of oxygen partial pressures of $10^2$–$10^5$ Pa ($10^{-3}$–1 atmosphere). In this manner a small contact surface of the electrodes with the solid electrolyte shifts the range towards higher values of the oxygen partial pressure.

The special feature of the present system is that the temperature range within which it can be used is much lower than in other systems, for example, $ZrO_2$ stabilised by $Y_2O_3$, and is so low that ageing has an immeasurably small effect. Moreover, the resistance as a function of the oxygen pressure shows a monotonous variation in contrast with other systems in which a minimum occurs within the measuring range.

The electrode coatings of the sensor according to the invention consists of noble metal, for example Pd or Au, but platinum is to be preferred. An advantage is also that the sensor according to the invention is suitable for miniaturisation.

As already noted above, in the sensor according to the invention, as in other systems, the disadvantage exists of the necessity of the use of a thermostat. This can be avoided, however, by measuring the electrolyte resistance with two alternating current frequencies, a low value (less than 100 Hz) and a high value (10 KHz or higher). The temperature can be determined by means of the impedance circle with which the real part and the imaginary part of the impedance is described. At the high frequency the circle intersects the axis and then gives the resistance of the electrolyte, at the low frequency the circle also intersects the axis and thus provides the value of the sum of electrolyte plus electrode. The value of the resistance at the high frequency can be plotted on a calibration curve as a function of the temperature. In this manner the temperature can be read, if desired by means of a reference curve stored in a microprocessor. In that case a thermocouple is not necessary in the sensor but, of course, a generator of the alternating voltage signal and possibly a microprocessor having a circuit coupled thereto are necessary.

The description of two constructions of an oxygen sensor according to the invention is now given by way of example.

EXAMPLE 1

A sintered tablet of the composition $$(Bi_2O_3)_{0.80}(Er_2O_3)_{0.20}$$

having a diameter of 0.7/μm and a thickness of 1.5 mm was provided with a 0.7/μm thick platinum layer on both major surfaces by sputtering. For this construction the value n in the above formula is $n = -\frac{1}{2}$.

At 700° C. the following values were measured:

| | |
|---|---|
| $R_{electrode}$ | (100% $O_2$) = 2.6Ω |
| $R_{electrode}$ | (1.6% $O_2$) = 22.3Ω |
| $R_{electrolyte}$ | 2.5Ω |
| K = 2.7 ± 0.1; and at 550° C. | |
| $R_{electrode}$ | (100% $O_2$) = 62Ω |
| $R_{electrode}$ | (1.6% $O_2$) = 420Ω |
| $R_{electrolyte}$ | 130Ω |
| K = 58/± 4. | |

EXAMPLE 2

A platinum gauze having 200 meshes/cm$^2$ was sandwiched between two tablets of the same composition as the tablet used in Example 1. For this construction a value of n = −⅔ holds in the above formula.

At 700° C. the following values were measured;

| | |
|---|---|
| $R_{electorde}$ | (100% $O_2$) = 73Ω |
| $R_{electrode}$ | (1.6% $O_2$) = 353Ω |
| $R_{electrolyte}$ | 5Ω |
| K = 74 ± 1; | | and at 550° C. the following values:

| | |
|---|---|
| $R_{electrode}$ | (100% $O_2$) = 1420Ω |
| $R_{electrode}$ | (1.6% $O_2$) = 5400Ω |
| $R_{electrolyte}$ | 490Ω |
| K = 1300 ± 100 | |

What is claimed is:

1. A sensor for determining oxygen content in a gas to be analyzed comprising
   at least one solid electrolyte of stabilized $Bi_2O_3$ in the form of a tablet, said tablet being located entirely in said gas to be analyzed, and said tablet having opposite major surfaces,
   an electrode coating at each said major surface of said tablet, and
   means for measuring resistance between said electrode coatings, said resistance being a monotonous variation of oxygen partial pressure of said gas to be analyzed,
   wherein said means for measuring resistance operates at two different alternating current frequencies, said two alternating current frequencies being a first frequency having a value of up to 100 Hz and being a second frequency having a value of at least 100 KHz.

2. A sensor according to claim 1, wherein said stabilized $Bi_2O_3$ consists of $Bi_2O_3$ with an addition of yttrium oxide, an oxide of an element from the lanthanide group having an atomic number from 62 to 70, niobium oxide, tantalum oxide, or tungsten oxide.

3. A sensor according to claim 1, wherein said stabilized $Bi_2O_3$ is a face-centered cubic lattice crystal structure.

4. A sensor according to claim 1, wherein said electrode coatings are platinum.

5. A sensor according to claim 1, wherein said electrode coatings are one of a guaze electrode coating or a sputtered electrode coating.

6. A sensor according to claim 1, wherein said means for measuring resistance operates at a constant temperature.

7. A sensor according to claim 1, wherein said means for measuring resistance operates in a temperature range from 500° C. to 800° C.

8. A sensor according to claim 1, wherein said means for measuring resistance operates at an oxygen partial pressure ranging from $10^{-3}$ to 1 atmosphere.

9. A sensor according to claim 1, wherein two of said tablets of the same composition are provided with a gauze electrode coating therebetween.

10. A sensor according to claim 9, wherein said gauze electrode coating is a platinum gauze having a mesh size of 200 meshes/cm$^2$.

11. A sensor according to claim 1, wherein said tablet has a diameter of 7 mm and a thickness of 0.7 mm.

12. A sensor according to claim 11, wherein said electrode coating is a 0.7 micron thick platinum layer, and said electrode coating is a sputtered electrode coating.

13. A measuring device comprising
    a solid electrolyte of stabilized $Bi_2O_3$ in the form of a tablet, said tablet being located entirely in a gas to be analyzed, and said tablet having opposite major surfaces,
    an electrode coating at each said major surface of said tablet,
    means for measuring resistance between said electrode coatings, said resistance being a monotonous variation of oxygen partial pressure of said gas to be analyzed,
    wherein said means for measuring resistance operates at two different alternating current frequencies, said two alternating current frequencies being a first frequency having a value of upto 100 Hz and being a second frequency having a value of at least 10 KHz,
    means for generating and applying alternating current to said tablet, and
    circuit means for providing a reference curve giving temperature of said tablet from said resistance.

14. A measuring device comprising
    a solid electrolyte of stabilized $Bi_2O_3$ in the form of a tablet, said tablet being located entirely in a gas to be analyzed, and said tablet having opposite major surfaces,
    an electrode coating at each said major surface of said tablet,
    means for measuring resistance between said electrode coatings at a first frequency of upto 100 Hz and at a second frequency of at least 10 KHz, and
    microprocessor means for providing temperature of said tablet from the measured resistance.

* * * * *